(12) United States Patent
Missotten et al.

(10) Patent No.: US 8,139,824 B2
(45) Date of Patent: *Mar. 20, 2012

(54) CROP PARTICLE DISCRIMINATION METHODS AND APPARATUS

(75) Inventors: Bart M. A. Missotten, Winksele (BE); Carmen S. Wallays, Izegem (BE)

(73) Assignee: CNH America LLC, New Holland, PA (US)

( * ) Notice: Subject to any disclaimer, the term of this patent is extended or adjusted under 35 U.S.C. 154(b) by 422 days.

This patent is subject to a terminal disclaimer.

(21) Appl. No.: 12/455,476

(22) Filed: Jun. 2, 2009

(65) Prior Publication Data

US 2009/0297040 A1    Dec. 3, 2009

(30) Foreign Application Priority Data

Jun. 2, 2008    (EP) ..................... 08010081

(51) Int. Cl.
*G06K 9/00*    (2006.01)
*G06K 9/62*    (2006.01)

(52) U.S. Cl. ....................... 382/110; 382/209

(58) Field of Classification Search .................. 382/100, 382/110, 209; 348/61, E7.085; 56/10.2 R, 56/220, 14.4, 14.6; 460/1, 4–7; 701/50, 701/207, 217; 356/326–328, 330–334, 343, 356/402–411; 193/2 R, 23; 198/307.1, 311, 198/350.11; 342/715; 73/861.71–861.74, 73/861.41, 73; 250/226, 227.11–227.27, 250/339.12, 339.02, 559.27, 910

See application file for complete search history.

(56) References Cited

U.S. PATENT DOCUMENTS

| 6,119,442 | A | 9/2000 | Hale | |
|---|---|---|---|---|
| 6,192,664 | B1* | 2/2001 | Missotten et al. | .......... 56/10.2 R |
| 6,826,967 | B2* | 12/2004 | Missotten et al. | .......... 73/861.73 |
| 7,771,262 | B2* | 8/2010 | Missotten | ..................... 460/114 |
| 2009/0074243 | A1* | 3/2009 | Missotten et al. | ............ 382/100 |
| 2009/0125197 | A1* | 5/2009 | Behnke | .......................... 701/50 |
| 2009/0258684 | A1* | 10/2009 | Missotten et al. | ................ 460/5 |

FOREIGN PATENT DOCUMENTS

| EP | 0826959 | 4/1998 |
|---|---|---|
| JP | 61065154 | 4/1986 |
| WO | WO 2006010761 | 2/2006 |

* cited by examiner

*Primary Examiner* — Samir Ahmed
*Assistant Examiner* — Mehdi Rashidian
(74) *Attorney, Agent, or Firm* — Michael G. Harms

(57) ABSTRACT

A method of discriminating between kernel and chaff particles, in crop, using a crop viewing apparatus that includes
an image-capturing device that is capable of capturing one or more images of crop in the crop viewing apparatus. The image capturing device connected to a processing device for processing one or more resulting images. The crop viewing apparatus also includes
one or more lamps for illuminating crop in the crop viewing apparatus. The lamp illuminates the crop in a range of illumination levels up to a maximal level equal to or above a reflectivity saturation level at which increasing illumination causes no further reflectivity change. The crop viewing apparatus further includes
one or more control devices for controlling the level of illumination provided by each lamp.

10 Claims, 3 Drawing Sheets

Reflectivity calculated with grey patch

Reflectivity calculated with mean intensity over image

Signal to noise ratio of the contrast between chaff and kernels for the different wavelengthband images at the different illumination levels

CROP PARTICLE DISCRIMINATION METHODS AND APPARATUS

CROSS REFERENCE TO RELATED APPLICATIONS

This Patent Application claims priority under 35 U.S.C. §119 to EP 08.010.081.1, filed on Jun. 2, 2008 titled, "CROP PARTICLE DISCRIMINATION METHODS AND APPARATUS" and having Bart M.A. Missotten and Carmen S. Wallays as inventors. The full disclosure of EP 08.010.081.1 is hereby fully incorporated herein by reference.

This invention relates to crop particle discrimination methods, especially such methods as are suitable for use in crop harvesting machines including but not limited to combine harvesters. The invention also relates to apparatus for performing such methods.

In WO-A-2006/010761 it is proposed for machines that harvest grains to include some form of "machine vision" for analysing the quality of crop being conveyed through the harvesting machine along one or more crop movement paths. An overall crop movement path extends from a forward end of the harvesting machine, where plant material together with various contaminants is ingested; to an intermediate storage tank and from there to a discharge chute on the side of the vehicle.

The interior machinery of a harvesting machine performs various functions the primary aim of which is to ensure that only valuable crop parts, i.e. kernels that may be used in food production or the production of e.g. biofuels, are discharged via the chute.

Depending on the plant type being harvested such machinery may also aim during harvesting to produce a good quality stream of a by-product, straw, that also has commercial value especially in markets in which the keeping of livestock, certain pets and horses is prevalent. The straw is discharged from the rear of the machine via a distinct path from the grain discharge chute. It is desirable for the stream of straw additionally to be as clean and unadulterated as possible.

There are various reasons why a user might wish to analyze crop quality based on images.

One of the more important is that the sub-systems of a harvesting machine such as a combine harvester include many adjustable components the adjustment of which can significantly influence the quality of crop. It is nearly always desirable to adjust such components in order to achieve the best crop quality possible without jeopardizing harvesting efficiency. However very often the quality of the crop in the machine cannot be analyzed by any means other than a visual one since the parts of the material ingested by the harvesting machine may be similar in terms of physical and/or chemical characteristics that might otherwise be measured electronically.

It is possible to consider in connection with harvesting on the one hand grains or kernels that have commercial value and on the other hand material other than grain or "MOG" that should be eliminated from the stream of processed material before the grains/kernels are discharged via the discharge chute and/or the straw is also discharged.

Various techniques exist for identifying, without operator intervention, certain types of MOG such as scrap metal and stones. One particular type of MOG however that presents acute identification problems is chaff, i.e. valueless parts of ingested plants. Such valueless parts may include husks, leaf parts and parts of stems.

Chaff is particularly difficult to identify since it is biologically and hence chemically similar to kernels and straw. Being harvested at the same time as the rest of the plant material it also frequently presents the same physical qualities such as moisture content, density and color.

Many designers and manufacturers of harvesting machines regard the use of machine vision as essential in assuring the quality of material processed in a harvesting machine. Until now however chaff has remained problematic when using machine vision apparatuses in harvesting machines.

This is because chaff parts such as husks may have shapes that are visually similar to kernels; and chaff typically reflects incident light in the same range of wavelengths as kernels and straw. Shape recognition algorithms and methods based on reflected light analyses therefore have been sub-optimal in identifying chaff.

It follows that there is a need for methods of discriminating between chaff and kernels that are better than the prior art techniques.

According to the invention in a first aspect there is provided a method of discriminating between kernel and chaff particles, in crop, using a crop viewing apparatus that includes:

a) an image-capturing device that is capable of capturing one or more images, each comprising a plurality of pixels, of crop in the crop viewing apparatus, the image capturing device being operatively connected to an image processing device for processing one or more resulting images;

b) one or more lamps for illuminating crop in the crop viewing apparatus, the or each said lamp being capable of illuminating the crop in a range of illumination levels up to a maximal level equal to or above a reflectivity saturation level; and c) one or more control devices for controlling the level of illumination provided by each said lamp, the method comprising the steps of:

d) operating at least one said control device to cause illumination of crop in the crop viewing apparatus at one or more levels less than the said reflectivity saturation level (also referred to herein as "under saturated illumination levels") so as to enhance differences in reflectivity between kernels and chaff in the crop viewing apparatus;

e) operating the image-capturing device while the crop is so illuminated to capture one or more crop images; and f) operating one or more said image processing devices in order to discriminate in the images between kernel and chaff particles based on their reflectivity characteristics at a said illumination level less than the saturation level.

It will be understood that the intensity of the light reflected by crop or other material varies with the intensity of the applied illumination. However, also the reflectivity, i.e. the ratio of the intensity of the reflected light to the intensity of the applied light, changes when the illumination changes between zero and the maximal level. The inventors have found that for each wavelength an intensity level can be identified above which no further substantial changes in reflectivity will be seen. This level is referred to as the "reflectivity saturation level". Illumination levels below this saturation level will be referred to as "undersaturated".

Advantageously the inventors have found that illuminating crop containing chaff at certain under saturated illumination levels increases the ability to discriminate between chaff on the one hand and grains on the other. This benefit is based on the discovery that despite numerous visual similarities chaff differs from kernels in terms of reflectivity. The inventors also have surprisingly found that such differences between the reflectivity of chaff and the reflectivity of kernels are most pronounced at illumination levels that in addition to being below the saturation level indicated above are far below the maximal levels that the lamps typically found in combine harvester machine vision systems are capable of generating.

The precise illumination levels at which the best discrimination is possible varies depending firstly on the plant type under investigation and secondly on the wavelength of the illuminating light. Since in some machine vision apparatuses used in combine harvesters there are multiple illumination lamps sequentially illuminating the crop in a range of wavelengths conveniently the method of the invention includes the step of, before operating at least one said control device, establishing the or each said illumination level less than the saturation level. In practical use of the method this step preferably is completed for a range of crop types and for a range of illumination light wavelengths.

Such an approach may result in a set of illumination data that may be analyzed in accordance with techniques specified herein in order to identify the best under saturated illumination levels for particular crop viewing apparatuses when employed to view specific crop types.

This may in turn lead to for example the creation of an illumination level database. Such a database may be used in conjunction with an automatic control program that may set the optimal levels of illumination of a plurality of differing wavelength output lamps of a viewing apparatus in a combine harvester when e.g. an operator inputs at the start of a harvesting session data identifying the type of crop to be harvested.

Conveniently the step of establishing the or each illumination level less than the maximal includes recording reflectivity characteristics of kernel and chaff particles; correcting the said reflectivity characteristics for spatial inhomogeneity of illumination at each of a series of illumination levels; and selecting the illumination level or the combination of illumination levels of the series providing the most pronounced difference in reflectivity between kernel and chaff of a crop type following such correction.

In practice the sub-step of recording the reflectivity characteristics of kernel and chaff particles involves comparing their reflection intensity levels, at differing illumination intensities, to a reference reflection intensity value. The reference reflection value may be obtained e.g. by illuminating a reflective strip or patch at the same intensity as the kernels and chaff. In one technique according to the invention the reflective strip or patch is colored grey so as to reflect a generally constant percentage of incident light regardless of its intensity.

Conveniently the step of correcting the reflectivity characteristics includes at each of the series of illumination levels determining the ratio of absolute reflection intensity of one or more individual pixels to a mean absolute reflection intensity of an entire image.

This technique has been found to provide good correction for any spatial inhomogeneity of illumination. This factor is significant since such spatial inhomogeneity tends to make the reflectivity of the kernels change, with changing illumination intensities, in a manner that is dissimilar to the change in reflectivity of chaff. If the effects of spatial inhomogeneity are eliminated the new reflectivity values of the kernels may become approximately constant over a range of illumination levels while the reflectivity characteristics of the chaff remain changeable over the range. As a result the differences in reflectivity that become apparent at low illumination intensities may be made more stark. This in turn makes it easier to identify the optimal under saturated illumination level for a particular crop when illuminated in light of a particular wavelength.

In more detail the step of correcting the reflectivity characteristics preferably includes at each of the series of illumination levels determining the ratio of absolute reflection intensity of one or more individual pixels to a mean absolute reflection intensity of an entire image. This technique has been found to be reliable and computationally straightforward to implement.

Instead of using a single image captured at an optimal illumination level and wavelength, the method may be improved by capturing at least one further crop image at least one further distinct wavelength and/or illumination level less than the saturation level. The image processing device or devices may then combine the captured images in order to maximize differences between kernels and chaff particles in the combination range. The use of images of the same sample under varying illumination allows the extraction of additional information that substantially improves the determination of chaff and kernels. In a computationally economical way, the image processing device may make for each pixel a linear combination of the reflectivities in the captured images.

It is also preferable that the step of establishing the or each illumination level less than the saturation level includes determining for a plurality of images of crop or for a plurality of combinations of images of crop a signal-to-noise (SNR) ratio calculated as the absolute value of the difference between the mean reflectivity of chaff and the mean reflectivity of kernels, divided by the sum of the standard deviations of the reflectivities of chaff and kernels; and selecting as the illumination level less than the saturation level the illumination level used in the image or in the combination of images that exhibits the highest SNR value.

The use of SNR values has been found to facilitate the identification of optimal undersaturated illumination levels.

Preferably the method may include the step of using a genetic algorithm to select one or more said illumination levels less than the saturation level.

Genetic algorithm techniques are in themselves well known as ways of selecting from "fuzzy" data the "best" (as judged according to criteria that may be programmed in to the algorithms) values from a dataset. The use of genetic algorithms therefore is particularly suitable in the method of the invention since the dataset may be large (amounting to reflectivity comparisons for a wide range of crop types over a wide range of illumination intensities at various wavelengths).

The above-described techniques for establishing the preferred undersaturated illumination levels as indicated are performed before operation of a control device forming part of or operatively connected to the viewing apparatus occurs.

Most practically all the steps aimed at establishing preferred sub-maximal illumination levels would take place during the design of the viewing apparatus. As a consequence the undersaturated illumination levels could be programmed into a programmable device forming part of or operatively connected to the viewing apparatus such that it would be necessary for an operator of a harvesting machine only to indicate (e.g. by selecting from a menu) the crop type being harvested. The illumination level most appropriate to the discrimination between kernels and chaff of the crop type in question could then be automatically set through the generation of appropriate control commands for the control device(s).

Regardless of the precise calculation philosophy adopted the method of the invention may optionally include the further steps of generating a control command in dependence on the outcome of the method; and transmitting the control command to an adjustable component or sub-system of a harvesting machine in which the viewing apparatus is included or to which the viewing apparatus is operatively connected in order to alter the setting of the adjustable component or sub-system.

This aspect of the method may advantageously be used for example to adjust an aspect of the kernel cleaning process in order to reduce the amount of chaff passed with the kernels to the grain tank.

In this regard it is of course the case that in a machine such as a combine harvester quanta of crop are repeatedly conveyed through the machine along the crop conveyance path. Therefore if as is commonly the case the image-capturing device is capable of capturing a sequence of crop images the method of the invention may provide feedback on a control action the aim of which is to reduce the amount of chaff discharged with the kernels.

Such a control action may as indicated above be initiated automatically, based on the result of the kernel-chaff discrimination completed as part of the method of the invention; or it may be initiated by a harvester operator. In the latter case for example a display device may indicate to the operator that the chaff levels are unacceptably high and that he should perform an adjustment. Following such an adjustment the operator could determine its success by monitoring subsequent information displayed via the display device.

The crop viewing apparatus may preferably be incorporated in or operatively connected to a combine harvester so as to assess ingested material in the crop conveyance path. Such an apparatus however could in the alternative be provided for example in static machinery intended to assess the quality of crop e.g. at a wholesaler's depot or at a weighing station.

In another aspect of the invention there is provided crop viewing apparatus including:
a) an image-capturing device that is operable to capture one or more images, comprising a plurality of pixels, of crop in the crop viewing apparatus;
b) a processing device, that processes resulting images, to which the image-capturing device is operatively connected;
c) one or more lamps for illuminating crop in the crop viewing apparatus, the or each said lamp being capable of illuminating the crop in a range of illumination levels up to a maximal level equal to or above a reflectivity saturation level; and
d) one or more control devices for controlling at least one said lamp, based on one or more control commands generated by the processing device, to illuminate the crop at a level, less than a said saturation level, so as to enhance differences in reflectivity between kernels and chaff in the crop viewing apparatus.

Such an apparatus may also optionally be connected as necessary to one or more programmable devices that generate other control commands, such as those relating to adjustment of adjustable components or sub-systems of the combine harvester, as required.

There now follows a description of preferred embodiments of the invention, by way of non-limiting example, with reference being made to the accompanying figures in which.

Figure 2:
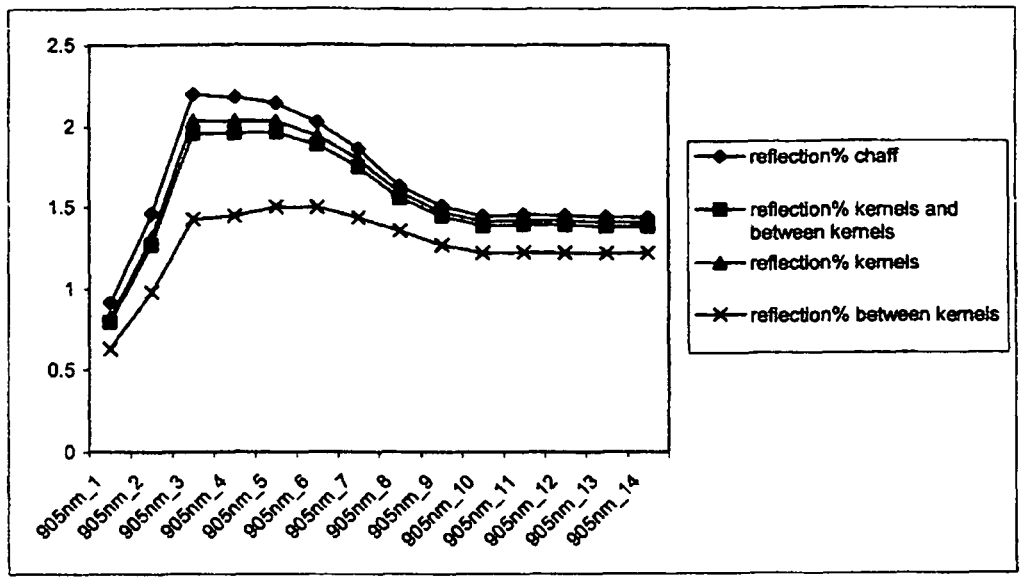
FIG. 2 is an exemplary plot of reflectivity of various components of a material stream, including crop, in a crop movement path such as that shown in FIG. 1 when illuminated at differing light intensities at a chosen wavelength.
Figure 3:
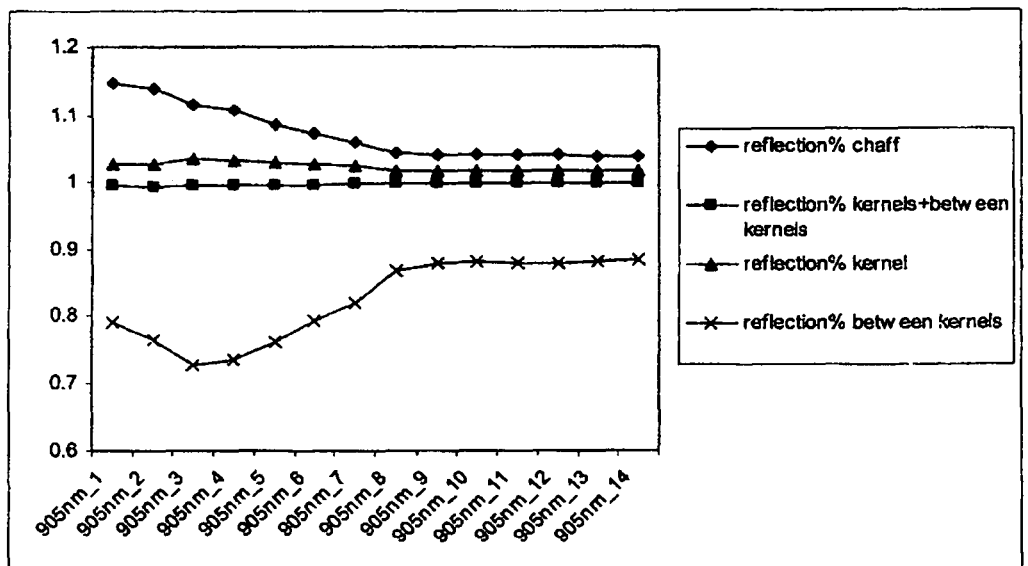
Figure 4:
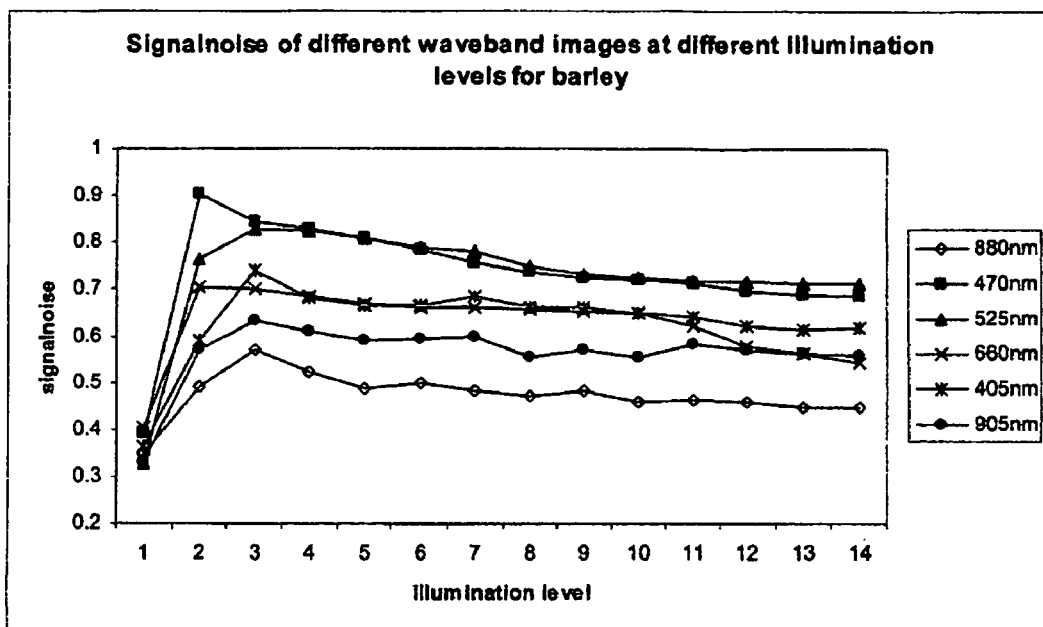

FIG. 3 is a plot of reflectivity of the same components of the material stream, when illuminated at the same light intensities and at the same wavelength as in FIG. 2, following correction of the reflectivity data for spatial inhomogeneity of illumination; and FIG. 4 is a plot of the SNR values of a sample of material in a crop movement path against differing illumination levels for a range of wavelengths of illumination.

Commonly, when referring to material processed by a combine harvester, the terms "grain", "straw", and "tailings" are used. The terms "chaff" and "broken grains" are also potentially relevant to the invention disclosed herein. These terms are not limiting.

"Grain" refers to that part of the crop (i.e. kernels) which is threshed and separated from the discardable part of the crop material; and "broken grains" as the term implies refers, to grains that are damaged or incomplete. The discardable part of the crop is referred to as MOG (Material Other than Grain), comprising "straw" and "chaff". As noted, MOG may also include various other contaminants that may be ingested at the forward end of a combine harvester. Incompletely threshed ears are referred to as "tailings".

The terms "forward", "rearward", "upper", "lower", "left", "right", etc when used in connection with a combine harvester and/or components thereof are determined with reference to the combine harvester in its normal operational condition and may refer either to the direction of forward operative travel of the combine harvester or to the direction of normal material flow through components thereof. Such terms should not be construed as limiting.

Figure 1:
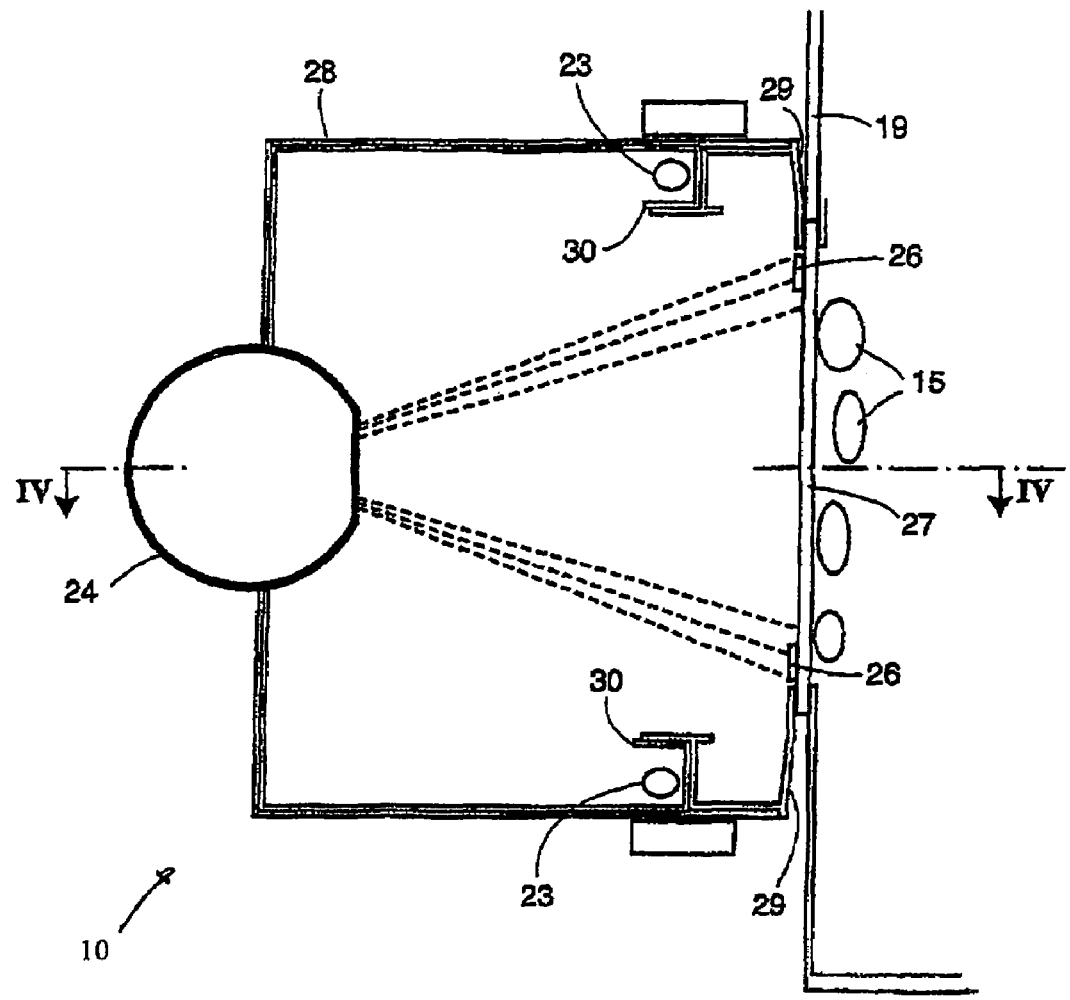
FIG. 1 is a schematic, sectioned view from above of a crop viewing or analysis apparatus that typically is provided in the interior of a combine harvester, adjacent a crop movement path.

As shown in FIG. 1 a crop viewing apparatus 10 according to the invention includes a light source represented schematically by lamps 23 that in the embodiment shown are light emitting diodes (LED's) (although other forms of lamp are possible within the scope of the invention). The light source is located to illuminate crop in a crop movement path. In the specific embodiments shown the location of the light source is such as to play light through a glass window 27 onto crop moving in the upright portion of housing 19 of a crop movement path in a combine harvester. The glass window 27 preferably is treated to be non-reflective, in order to eliminate the effects of stray reflections of light source 23. The crop side of the window should have low adhesive characteristics for the crop and MOG and be sufficiently resistant to scratches. This may be realised by a proper choice of transparent coating.

In the illustrated embodiment several series of the LED's are arranged around the periphery of a housing in the form of a box 28. The LED's lie in a gutter 30 as described below.

Each LED of a said series emits light at a predetermined wavelength (or in a narrow wavelength range centred on the predetermined wavelength). Since there are plural series of the LED's it is possible by controlling the switching of the LED's to choose the wavelength(s) of light by which crop is illuminated.

The apparatus of the invention additionally includes an image capturing device in the form of camera 24 (including a lens) that is arranged to capture sequential images of crop moving in the crop movement path. The images are taken through the glass window 27. The light source 23 may be arranged along the circumference of the window 27 and may shine its light on the interior of the box 28 that holds the camera 24, that preferably is a CCD (charge-coupled device). The walls of the box 28 reflect the light and provide a diffuse illumination on the crop material in the housing 19.

In FIG. 1 therefore there is shown a typical crop viewing apparatus 10 comprising a parallelepiped box 28 having a non-reflective glass window 27, which is mounted by way of a rubber seal 29 adjacent the crop movement path. Along the edge of the window 27, the box has a gutter 30 provided with a range of LED's, which constitute a light source 23. The LED's are directed so as to shine light into the interior of the box 28, which is coated with a layer of diffuse reflective paint. The gutter 30 prevents the LED's from shining directly upon the kernels 15 and other matter in the crop sensing area. In this manner the crop material is illuminated in a substantially uniform manner. The border of the window has an optional reference strip 26, the use of which will be described in further detail hereinafter.

The camera may have a built-in Digital Signal Processor, which is programmable to treat the images captured by the CCD elements. The intensity of illumination provided by the LED's is in each case controllable from a zero level up to the maximum output of each LED. The LED output intensity and the switching of the LED's may be controlled by e.g. a programmable device that is operatively connected to the apparatus 10.

In operation the CCD camera 24 captures series of images for the purpose of crop analysis. As explained hereinabove it is desirable to be able to discriminate between chaff and kernels in the images. However as also explained there are particular problems in performing such discrimination when using image processing techniques of the prior art.

The inventors however have realised that these problems may be overcome by considering the reflectivity differences that exist between kernels on the on hand and chaff on the other.

This is illustrated by FIG. 2, which is a plot of reflectivity (y-axis) of various crop parts (grain kernels and chaff) and the spaces between the kernels at differing light illumination levels (x-axis) ranging from a minimum labeled '1' (illumination level just above 0) in FIG. 2 to a maximal value (i.e. the maximum illumination level of which the lamps 23 controllably are capable).

FIG. 2 shows the results of reflectivity comparisons for a particular crop type, (wheat) when illuminated in light of a wavelength of 905 nm. The plots for other crop types (e.g. barley) and other illumination wavelengths are similar. The reflectivity values are determined by dividing the intensity of the light reflected from the crop by the intensity of the light reflected from the reference strip 26. The graph shows that the reflectivities of kernels and chaff vary substantially at lower illumination levels and remain substantially constant at higher illumination levels (above level 9). The illumination level above which changes in illumination effect no substantial changes in reflectivity of the crop will further be referred to as a "saturation illumination level".

FIG. 2 shows that the reflectivity of chaff is the highest of the crop parts considered. Kernels exhibit the next-highest reflectivity level. FIG. 2 also considers both a "composite" reflectivity mode constituted by reflections from a mixture of kernels and the spaces between kernels; and it also shows that such spaces on their own have comparatively low reflectivity levels. However the spaces do not significantly affect the total amount of light reflected, mainly because they make up only a small fraction of the image.

This in turn means that it is possible, when practicing the method of the invention, to use analysis algorithms that do not discriminate between the kernels and the spaces. This saves on the requirements of the digital signal processor since it is then necessary only to consider "chaff" (and other MOG) and "non-chaff" discriminations.

FIG. 2 illustrates, significantly, that, at a wavelength of 905 nm, all the reflectivity levels increase at illumination levels less than the saturation illumination value. This means that the ability to discriminate between chaff and non-chaff regions of each sequential image is enhanced at illumination levels below saturation illumination in ways that are not apparent at higher levels.

Similar plots for the reflectivity of chaff, kernels and spaces have been made for various wavelengths between 405 nm and 905 nm. At wavelengths generally above 650 nm the reflectivity values give rise to plots similar to those of FIG. 2: and at illumination levels below reflectivity saturation, the reflectivities of both chaff and kernels have values exceeding the reflection values obtained above the saturation level. At wavelengths generally between 650 nm and 500 nm the reflectivity of chaff has greater values below the saturation level, while the reflectivity of kernels has greater values above the same limit. At wavelengths generally below 500 nm the reflectivity values of both chaff and kernels have smaller values for illuminations below the saturation illumination.

Nevertheless all plots display a similar behavior for the difference between the reflectivity of the chaff and the reflectivity of the kernels (or kernels and spaces). As exemplified in FIG. 2, this difference reaches a maximum in the "low illumination" half of the plot, decreases towards the saturation illumination and remains substantially constant for illumination values that exceed the saturation value. This difference is indicative of the contrast between the grain and chaff and provides a further means for distinguishing between both in crop images.

When gradually decreasing the illumination level from the saturation value, the difference in reflectivity between chaff and kernels (or kernels and spaces) will increase first and then decrease when the illumination is approaching zero. The illumination level at which the difference is maximal, and hence the contrast is most noticeable, is the optimal level for the given wavelength. This optimal illumination level is not the same for each of the wavelengths, or for each of the crop types.

An important reason for the difference in reflection by chaff or kernels is that chaff tends to be flatter than kernels and therefore reflects light more coherently. The image of a crop sample is taken while it is loaded against the window 27. The chaff particles in the image take a position generally parallel to the window and perpendicular to the camera, thereby reflecting more light than the convex surfaces of the kernels. When the illumination is attenuated the reflection caused by the convex kernels diminishes more dramatically than the reflection caused by the flatter chaff.

By carrying out illumination tests for a range of crops at a range of illumination levels and wavelengths the result is a dataset from which it is possible to identify the optimal wavelength and illumination levels for particular crop types. Such data may be stored e.g. in the memory of a programmable device forming part of or connected to the control sub-systems of a combine harvester. An operator may then simply, during use of the combine harvester, indicate to the programmable device (e.g. by operating an input device such as a keypad or touch-screen menu) the crop type being harvested; and the programmable device may then generate commands that cause the lamps 23 to produce the optimal illumination characteristics for chaff discrimination in the crop in question.

For each crop sample, the system may take a series of images while varying the wavelengths and the intensity of the illumination. The reflection data per image pixel may then be combined, e.g. by multiplying the reflection values with a (canonical) coefficient and summing these products in order to generate a new image with enhanced distinction between chaff and kernels. The new image may also be created using a non-linear combination of the monochrome images.

Selection of the optimal illumination characteristics and of the optimal combination parameters may be achieved, typically at the stage of designing the control programs of the viewing apparatus 10, through the use of genetic algorithms (including but not limited to Canonical Discriminant Analysis) that are well known per se and are not described herein in detail. Other software and non-software techniques can be employed in order to identify the optimal illumination characteristics.

During such design steps the camera 24 takes images of a small number of crop samples at various wavelengths and at various illumination levels. In these images, the pixels pertaining to MOG and to the kernels are identified by an operator or by an independent system and the genetic algorithm is then used to trace the best-performing combination of images, i.e., the combination which yields the best contrast between MOG and kernels. The best wavelengths, illumination levels and combination parameters (e.g., canonical coefficients in a linear combination) are then retained for validation on further samples of the same crop. If they prove effective, they are loaded into the system and used for analysis of further samples of the same crop type.

Automatic crop recognition is also possible such that inputting of crop type data is not necessary for the performance of the method of the invention. Various techniques exist for achieving this, as are known to those of skill in the art. For instance, an imaging system may derive the crop type from characteristics such as color, size, shape and other morphological features.

The discrimination between non-chaff parts of an image and chaff can be further enhanced, at such low illumination levels, by compensating for the spatial inhomogeneity of illumination of the particles making up the image.

The inventors have found that this may be achieved by calculating the relationship between the absolute reflection of the crop pixels and the mean absolute reflection of the whole image. In this approach no more use has to be made of the reflection values of the reference strip 26.

The effect of such a manipulation is shown in FIG. 3, in which as a result of processing in order to eliminate the effects of spatial inhomogeneity the reflectivity of the kernels (and indeed the combined kernels and spaces between kernels) is rendered essentially constant across the whole range of illumination intensity levels. This is because kernels constitute the major portion of the image.

The FIG. 3 graph shows that the thus-normalized reflectivity of the chaff increases for decreasing illumination levels. The plot is representative of the behavior of the difference in reflectivity between chaff and kernels discussed above.

This makes it considerably computationally easier, when illuminating the crop in light of the optimal sub-maximal intensity, to identify chaff since it is necessary then only to identify pixels exhibiting a significant deviation in reflectivity levels from a normalized value representing the reflectivity of kernels.

FIG. 4 plots the SNR (signal to noise ratio) as defined herein for a particular crop type (barley in the example shown, although the principle is equally valid for other crop types) against the illumination intensity level at different wavelengths. FIG. 4 shows that for each wavelength there exists a distinct, optimal, under saturated illumination level. This information may be helpful in devising a control philosophy for the lamps 23 in the crop viewing apparatus.

In this regard if, for the sake of example when viewing barley the lamps emitting light at the wavelength 470 nm are chosen, it is obvious that an intensity level corresponding to an x-axis value in FIG. 4 of slightly less than 2 is optimal. If however during use of the crop viewing apparatus the LED lamps 23 that emit light in this wavelength fail, as may happen, in sufficient numbers such that it ceases to be possible to provide this level of illumination intensity as illustrated by FIG. 4, the reflectivity at 470 nm would dramatically tail away towards zero.

Such a condition may render operation of the crop viewing apparatus impractical for the purpose of chaff discrimination but it would then be possible to control the remaining lamps 23 so as to compensate for this effect.

Thus, for example, in the event of such lamp failure it would be possible to switch off the 470 nm LED lamps 23 and instead switch on the 405 nm lamps which as shown by FIG. 4 still exhibit good discrimination characteristics.

However the dataset obtained for barley suggests that the optimal sub-maximal illumination level at this wavelength corresponds to an x-axis value of approximately 2.5. Based on this knowledge the programmable device could generate control commands that permit continued operation of the crop viewing apparatus to discriminate chaff even in the event of lamp failure as described.

As indicated above, better discrimination between chaff and kernel pixels can be achieved by combining, e.g. by applying a canonical variable to, images taken at various wavelengths and at various illumination levels. The inventors have found that better discrimination models for both wheat and barley combined high illumination levels for 405 nm and 660 nm with low levels for 470 nm and 880 nm.

Since it is possible to adjust various adjustable parts of a combine harvester in dependence on control commands developed in a programmable device the discrimination technique of the invention may be used at least partially to control such adjustable parts.

As an example it is possible to provide a control regime that adjusts various parts of the combine harvester automatically so as to reduce the amount of chaff in the crop passing the crop viewing device to an economically acceptable low level. The method of the invention may also provide feedback inputs in the form of signals related to the detected quantities of chaff per unit time that can be used by a controller to fine-tune the various adjustments of threshing and cleaning systems and thereby improve grain quality.

As mentioned above the apparatus 10 may if desired include a reference strip 26 that typically would be a grey strip. This may be used for determining the reflectivity of crop parts in the image as described above, but it may also be used for the purpose of calibrating the apparatus of the invention e.g. during a set-up operation in a factory, by providing a "standardised" reflectivity characteristic in the absence of crop material from the vicinity of the apparatus 10. An alternative way of calibrating the apparatus 10 would involve passing synthetic, e.g. plastic, kernels along the crop movement path so as to provide images the reflectivity characteristics of which would be known in advance. The worker of skill in the art would readily know how to achieve calibration of the apparatus using either of the aforementioned techniques.

The invention claimed is:
1. A method of discriminating between kernel and chaff particles, in crop, using a crop viewing apparatus that includes:
  a) an image-capturing device that is capable of capturing one or more images, each comprising a plurality of pixels, of crop in the crop viewing apparatus, the image capturing device being operatively connected to an image processing device for processing one or more resulting images;

b) one or more lamps for illuminating crop in the crop viewing apparatus, the or each said one lamp being capable of illuminating the crop in a range of illumination levels up to a maximal level equal to or above a reflectivity saturation level; and c) one or more control devices for controlling the level of illumination provided by each said lamp, the method comprising the steps of d) operating at least one said control device to cause illumination of crop in the crop viewing apparatus at one or more level less than the said reflectivity saturation level so as to enhance differences in reflectivity between kernels and chaff in the crop viewing apparatus, and before operating at least one said control device, establishing the or each said one illumination level less than the saturation level, wherein the step of establishing the or each illumination level less than the saturation level includes:

determining for a plurality of images of crop or for a plurality of combinations of images of crop a signal-to-noise (SNR) ratio calculated as the absolute value of the difference between the mean reflectivity of chaff and the mean reflectivity of kernels, divided by the sum of the standard deviations of the reflectivities of chaff and kernels; and selecting as the illumination level less than the saturation level the illumination level used in the image or in the combination of images that exhibits the highest SNR value;

e) operating the image-capturing device while the crop is so illuminated to capture one or more crop images; and f) operating one or more said image processing devices in order to discriminate in the image between kernel and chaff particles based on their reflectivity characteristics at a said illumination level less than the saturation level.

2. A method according to claim 1 wherein the at least one processing device establishes the reflectivity as the ratio of the reflection intensity by the kernels or chaff to the reflection intensity by a reference strip.

3. A method according to claim 1 wherein the at least one processing device establishes the reflectivity as the ratio of the reflection intensity by the kernels or chaff to the mean reflectivity of the illuminated crop in the entire captured image.

4. A method according to claim 1 further comprising:
operating the at least one said control device to cause illumination of crop at least one further distinct wavelength and/or illumination level less than the said reflectivity saturation level; and
operating the image-capturing device while the crop is so illuminated to capture at least one further crop image;
wherein the step of operating one or more image processing devices comprises:
operating one or more image processing devices to combine at least two of the captured images in order to maximize differences between kernel and chaff particles in the combination image.

5. A method according to claim 4, wherein the image processing device or devices make for each pixel a linear combination of the reflectivities in at least two of the captured images.

6. A method according to claim 1 wherein the step of establishing the one or each illumination level less than the saturation level includes:
recording reflectivity characteristics of kernel and chaff particles;
correcting the said reflectivity characteristics for spatial inhomogeneity of illumination at each of a series of illumination levels; and
selecting the illumination level or the combination of illumination levels of the series providing the most pronounced difference in reflectivity between kernel and chaff of a crop type following such correction.

7. A method according to claim 1, wherein the step of establishing the one or each illumination level less than the saturation level includes:
recording reflectivity characteristics of kernel and chaff particles at a plurality of illumination levels at a plurality of wavelengths;
correcting the said reflectivity characteristics for spatial inhomogeneity of illumination;
generating combinations of the corrected reflectivity characteristics at said plurality of illumination levels and of wavelengths, and
selecting for each wavelength the illumination level of the series used in the generated combination providing the most pronounced difference in reflectivity between kernel and chaff of a crop type.

8. A method according to claim 6 wherein the step of correcting the reflectivity characteristics includes at each of the series of illumination levels determining the ratio of absolute reflection intensity of one or more individual pixels to a mean absolute reflection intensity of an entire image.

9. A method according to claim 1 including the step of using a genetic algorithm to select one or more said illumination levels less than the saturation level.

10. A method according claim 1 including the further steps of:
generating a control command in dependence on the outcome of the method; and
transmitting the control command to an adjustable component or sub-system of a harvesting machine in which the viewing apparatus is included or to which the viewing apparatus is operatively connected in order to alter the setting of the adjustable component or sub-system.

* * * * *